US00PP29417P3

(12) United States Plant Patent
Smit

(10) Patent No.: US PP29,417 P3
(45) Date of Patent: Jun. 19, 2018

(54) ***PEPEROMIA* PLANT NAMED 'SUNRISE'**

(50) Latin Name: ***Peperomia* hybrid**
Varietal Denomination: Sunrise

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days. days.

(21) Appl. No.: 15/330,448

(22) Filed: Sep. 22, 2016

(65) Prior Publication Data

US 2018/0084698 P1 Mar. 22, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS

UPOV-PLUTO: Plant Variety Database, citation for 'Sunrise', Retrieved from the Internet on Nov. 6, 2017. (1 page total).*

* cited by examiner

*Primary Examiner* — Susan McCormick Ewoldt

(57) ABSTRACT

A new cultivar of *Peperomia* plant named 'Sunrise' that is characterized by grey-green leaves with green veins on the upper surface, pink-red leaves on the lower surface, pink-red petioles and pink-red peduncles.

1 Drawing Sheet

Botanical classification: *Peperomia* hybrid.
Variety denomination: 'Sunrise'.

BACKGROUND OF THE INVENTION

The present invention relates to a new and distinct cultivar of *Peperomia* plant botanically known as *Peperomia* hybrid and hereinafter referred to by the cultivar name 'Sunrise'.

'Sunrise' originated from the self-pollination of an unnamed *Peperomia* hybrid cultivar. The crossing was conducted in 2013 in Sappemeer, Netherlands. The resulting seeds were subsequently planted and grown. The cultivar 'Sunrise' was selected by the inventor in 2014 in a controlled environment as a single plant within the progeny of the stated cross in a cultivated area of Sappemeer, Netherlands.

Asexual reproduction of the new cultivar 'Sunrise' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Sunrise'. These traits in combination distinguish 'Sunrise' as a new and distinct cultivar apart from other existing varieties of *Peperomia* known by the inventor.

1. *Peperomia* 'Sunrise' exhibits grey-green leaves with green veins on the upper surface and pink-red leaves on the lower surface.
2. *Peperomia* 'Sunrise' exhibits pink-red petioles and peduncles.

The closest comparison cultivars are *Peperomia* 'Eden Rosso' (U.S. Plant Pat. No. 24,379) and *Peperomia* 'Napoli Nights' (co-pending U.S. Plant patent application Ser. No. 15/330,400). 'Sunrise' is distinguishable from 'Eden Rosso' by the following characteristics:

1. *Peperomia* 'Sunrise' exhibits grey-green leaves with green veins on the upper surface. In comparison, the upper leaf surface of 'Eden Rosso' is darker green in color.
2. The leaves of *Peperomia* 'Sunrise' are more oval shaped than the leaves of 'Eden Rosso'. In comparison, the leaves of 'Eden Rosso' are more elongated and pointed in shape.

'Sunrise' is distinguishable from 'Napoli Nights' by the following characteristics:

1. *Peperomia* 'Sunrise' exhibits grey-green leaves with green veins on the upper surface. In comparison, the upper leaf surface of 'Napoli Nights' is more grey in color.
2. *Peperomia* 'Sunrise' exhibits leaves that are larger in size than the leaves of 'Napoli Nights'.

'Sunrise' is distinguishable from the parent plant, by the following characteristics:

1. The leaves of 'Sunrise' are grey-green on the upper surface. The leaves of the parent plant are darker grey-green on the upper surface.
2. The leaves of 'Sunrise' are pink-red on the lower surface. The leaves of the parent plant are pink-green on the lower surface.
3. The leaves of *Peperomia* 'Sunrise' are more oval shaped than the leaves the parent plant. In comparison, the leaves of the parent plant are more elongated and pointed in shape.

BRIEF DESCRIPTION OF THE DRAWING

The accompanying photograph illustrates the distinguishing traits of *Peperomia* 'Sunrise'. The photograph shows an overall view of a 30 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Sunrise'. Data was collected in Sappemeer, Netherlands from 30 week old plants grown in a glass greenhouse in 10.5 cm. diameter containers. The time of year was Summer and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Sunrise' has not been tested under all possible conditions and phenotypic differences may be observed with variations in environmental, climatic, and cultural conditions, however, without any variance in genotype.

Botanical classification: *Peperomia* hybrid 'Sunrise'.
Annual or perennial: Perennial.
Parentage: 'Sunrise' is a self-crossing of an unnamed *Peperomia* hybrid cultivar.
Plant type: Potted plant.
Growth habit: Rosette.
Plant shape: Flattened globe shaped.
Suitable container size: 10.5 cm. pots or larger.
Plant height: 15.3 cm.
Plant width: 27.0 cm.
Vigor: Low.
Low temperature tolerance: 10° Centigrade.
High temperature tolerance: 35° Centigrade.
Propagation: Leaf cuttings.
Time to initiate roots (summer): 10 days at 18 to 20° C.
Time to initiate roots (winter): 14 days at 18 to 20° C.
Time to produce a rooted cutting (summer): 80 days at 18 to 20° C.
Time to produce a rooted cutting (winter): 100 days at 18 to 20° C.
Growth rate: Low.
Crop time: Approximately 18 to 22 weeks in Sappemeer, Netherlands.
Root system: Fibrous.
Plant fragrance: None.
Stem:
- *Branching habit.*—Short thick stems branching into rosettes of leaves.
- *Number of main stems per plant.*—Average 15.
- *Number of lateral branches per plant.*—Average 45.
- *Lateral branch dimensions.*—0.4 cm. in length and 0.6 cm. in width.
- *Internode length.*—0.1 cm.
- *Stem shape.*—Rounded.
- *Stem texture.*—Smooth.
- *Stem pubescence.*—Absent.
- *Stem angle.*—10 degrees.
- *Stem strength.*—Moderately strong.
- *Stem color* (*young*).—176A.
- *Stem color* (*mature*).—176A.
- *Internode color.*—176A.

Foliage:
- *Leaf arrangement.*—Alternate.
- *Compound or single.*—Single.
- *Quantity of leaves per lateral branch.*—Average 5.
- *Leaf shape.*—Ovate.
- *Leaf aspect.*—Moderately convex.
- *Leaf apex.*—Broad acute.
- *Leaf base.*—Cordate.
- *Leaf dimensions.*—5.9 cm. in length and 4.5 cm. in width.
- *Texture.*—Glabrous (both surfaces).
- *Leaf luster.*—Upper surface glossy, lower surface matte.
- *Pubescence.*—Absent.
- *Leaf margin.*—Entire.
- *Venation pattern.*—Parallel, strongly furrowed.
- *Young leaf color* (*upper surface*).—Between N189C and 198A, surrounding veins N189A.
- *Young leaf color* (*lower surface*).—183C, surrounding veins 183A.
- *Mature leaf color* (*upper surface*).—Between N189B and N189C.
- *Mature leaf color* (*lower surface*).—182B.
- *Vein color* (*upper surface*).—Varies between 139A and N189A.
- *Vein color* (*lower surface*).—183A.

Petiole:
- *Petiole dimensions.*—8.2 cm. in length and 0.35 cm. in diameter.
- *Petiole texture.*—Glabrous.
- *Petiole luster.*—Slightly glossy.
- *Petiole pubescence.*—Absent.
- *Petiole strength.*—Low.
- *Petiole color.*—N170D with fine stripes 182A.

Flower:
- *Inflorescence type.*—Axillary spike.
- *Inflorescence dimensions.*—4.8 cm. in length and 0.25 cm. in diameter.
- *Quantity of flowers per inflorescence.*—Average 600.
- *Quantity of flowers and buds per plant.*—Average 12,000.
- *Fragrance.*—None.
- *Bud length.*—Average 0.2 mm.
- *Bud diameter.*—Average 0.2 mm.
- *Bud shape.*—Globose.
- *Bud color.*—143A.
- *Flower type and form.*—Flowers have no petals and consist of two stamens and a single pistil.
- *Flower aspect.*—Outward.
- *Flower dimensions.*—Average 0.5 mm. in diameter and 0.3 mm. in height.
- *Flower longevity.*—Approximately 1 month.
- *Persistent or self-cleaning.*—Self-cleaning.

Peduncle:
- *Peduncle dimensions.*—8.5 cm. in length and 0.2 cm. in diameter.
- *Peduncle angle.*—30 degrees from vertical.
- *Peduncle strength.*—Moderately weak.
- *Peduncle texture.*—Smooth.
- *Peduncle luster.*—Glossy.
- *Peduncle color.*—180A.

Reproductive organs:
- *Stamen number.*—2.
- *Anther shape.*—Club shaped.
- *Anther length.*—0.1 mm.

*Anther color.*—145D.
*Filament length.*—0.1 mm.
*Filament color.*—144C.
*Amount of pollen.*—Low.
*Pollen color.*—155A.
*Number of pistils.*—1.
*Pistil length.*—0.05 mm.
*Stigma shape.*—Flattened, ovate.
*Stigma dimensions.*—0.05 mm. in length and 0.2 mm. in diameter.
*Stigma color.*—143C.
*Style.*—None visible.
*Ovary color.*—144A.

Fruit and seed: 'Sunrise' has not produced fruit or seed to date.

Disease and pest resistance: Disease and pest resistance has not been observed.

The invention claimed is:

1. A new and distinct variety of *Peperomia* plant named 'Sunrise' as described and illustrated.

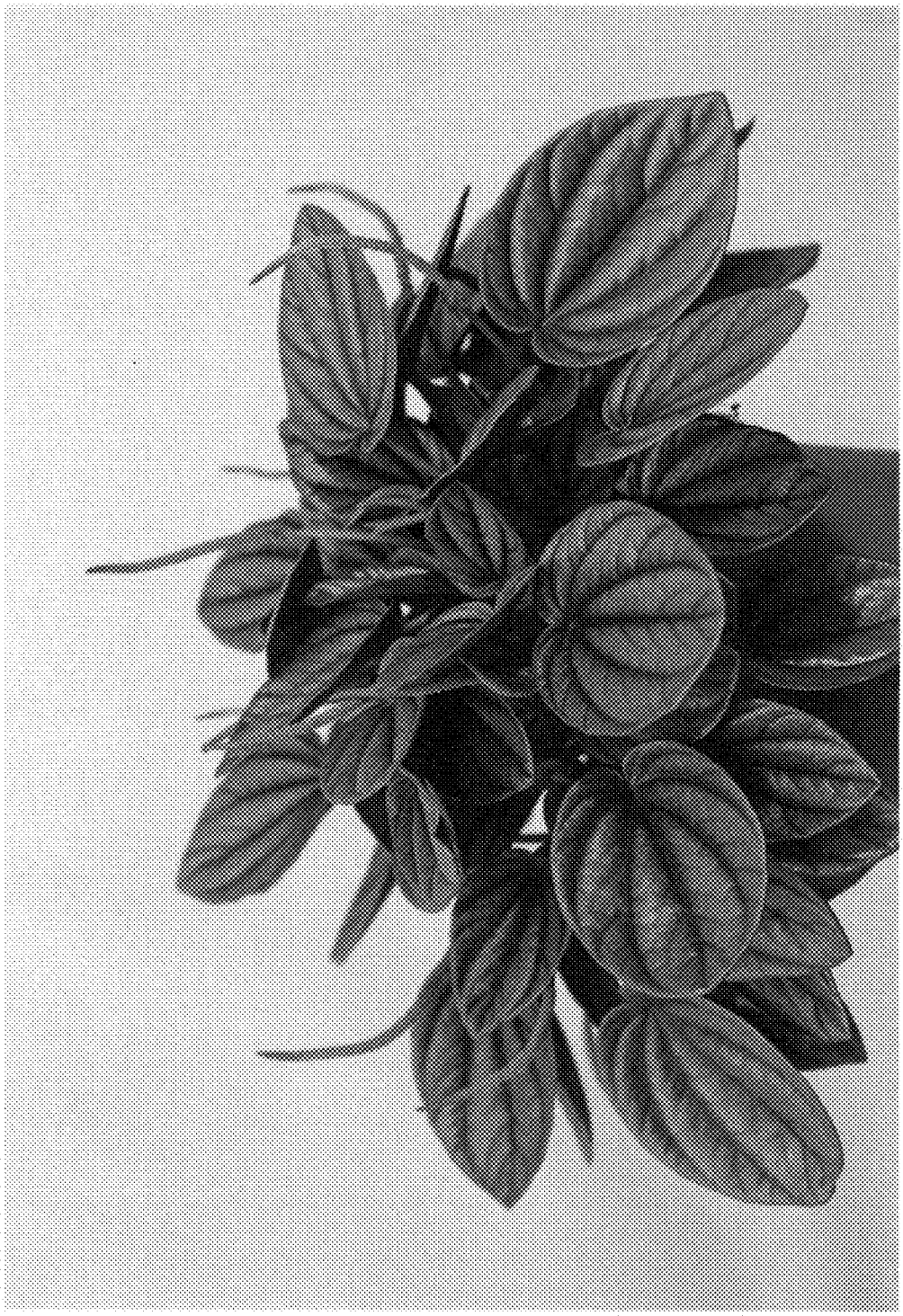

* * * * *